US008528728B2

(12) United States Patent
Pugh et al.

(10) Patent No.: US 8,528,728 B2
(45) Date of Patent: Sep. 10, 2013

(54) OPHTHALMIC LENS DISINFECTING STORAGE CASE

(75) Inventors: Randall B. Pugh, Jacksonville, FL (US); Edward R. Kernick, Jacksonville, FL (US); William Chester Neeley, Melbourne, FL (US); Dwight Abouhalkah, Jacksonville, FL (US); Leslie A. Voss, Jacksonville, FL (US); Karson S. Putt, Jacksonville, FL (US); James Daniel Riall, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 13/095,805

(22) Filed: Apr. 27, 2011

(65) Prior Publication Data
US 2011/0284396 A1    Nov. 24, 2011

Related U.S. Application Data

(60) Provisional application No. 61/346,152, filed on May 19, 2010.

(51) Int. Cl.
*A45C 11/00*      (2006.01)
(52) U.S. Cl.
USPC ..................................... 206/5.1; 250/455.11
(58) Field of Classification Search
USPC .............. 206/5, 5.1, 210; 134/184, 186, 137, 134/901; 250/455.11
See application file for complete search history.

(56) References Cited

U.S. PATENT DOCUMENTS

| 3,852,032 | A |   | 12/1974 | Urbach |          |
|-----------|---|---|---------|--------|----------|
| 3,978,341 | A |   | 8/1976  | Hoell  |          |
| 4,063,890 | A |   | 12/1977 | Baron  |          |
| 4,392,569 | A | * | 7/1983  | Shoup  | 206/5.1  |
| 4,415,076 | A | * | 11/1983 | Campbell | 206/5.1 |
| 4,444,307 | A | * | 4/1984  | Jermyn | 206/5.1  |
| 4,545,479 | A | * | 10/1985 | Figari | 206/5.1  |
| 4,782,946 | A | * | 11/1988 | Pollak | 206/223  |
| 4,858,754 | A | * | 8/1989  | Wright et al. | 206/5.1 |
| 4,868,397 | A |   | 9/1989  | Tittel |          |
| 4,897,981 | A | * | 2/1990  | Beck   | 53/431   |
| 5,086,913 | A | * | 2/1992  | Camm et al. | 206/5.1 |
| 5,120,499 | A |   | 6/1992  | Baron  |          |
| 5,144,144 | A |   | 9/1992  | Borovsky |        |

(Continued)

FOREIGN PATENT DOCUMENTS
FR    2 369 847 A1    6/1978
JP    2002126050 A    5/2002
JP    2003093481 A    4/2003

OTHER PUBLICATIONS

Harris, M.G., et al. "Ultraviolet disinfection of contact lenses." *Optometry and Vision Science*, Oct. 1993;70(10): 839-42. Print.

(Continued)

*Primary Examiner* — David Fidei

(57) ABSTRACT

The present invention for a storage case for an ophthalmic lens, wherein the storage case facilitates disinfecting of the ophthalmic lens with disinfecting radiation. Various embodiments may include an alignment device, such as a pedestal or a concave bowl to position the lens to receive disinfecting radiation. In addition, the case may include one or more disinfecting radiation windows for admitting disinfecting radiation into the storage case.

13 Claims, 4 Drawing Sheets

(56) References Cited

U.S. PATENT DOCUMENTS

| | | | |
|---|---|---|---|
| 5,407,062 A * | 4/1995 | Shannon et al. | 206/5.1 |
| 5,439,642 A | 8/1995 | Hagmann | |
| 5,474,169 A * | 12/1995 | Bauman | 206/5.1 |
| 5,618,492 A | 4/1997 | Auten | |
| 6,030,554 A | 2/2000 | Ichihara | |
| 6,044,966 A * | 4/2000 | Haase | 206/5.1 |
| 6,365,111 B1 * | 4/2002 | Bass | 422/547 |
| 6,461,568 B1 | 10/2002 | Eckhardt | |
| 6,592,816 B1 | 7/2003 | Ebel | |
| 6,756,350 B1 * | 6/2004 | Giblin et al. | 510/277 |
| 6,790,409 B1 | 9/2004 | Nakamura | |
| 7,217,936 B2 | 5/2007 | Ressler | |
| 7,879,288 B2 | 2/2011 | Brown-Skrobot | |
| 2004/0234569 A1 | 11/2004 | Nakada | |
| 2005/0013729 A1 | 1/2005 | Brown-Skrobot | |
| 2005/0028848 A1 | 2/2005 | Lai | |
| 2005/0173652 A1 | 8/2005 | Ressler | |
| 2006/0011496 A1 * | 1/2006 | Mangabeira Nunez | 206/5.1 |
| 2007/0104611 A1 | 5/2007 | Marmo | |
| 2007/0206377 A1 | 9/2007 | Borup | |
| 2007/0261970 A1 * | 11/2007 | Stull | 206/5.1 |
| 2007/0267444 A1 * | 11/2007 | de Buzzaccarini et al. | 222/179.5 |
| 2009/0086160 A1 | 4/2009 | Enns | |
| 2009/0274576 A1 | 11/2009 | Ressler | |
| 2010/0183996 A1 * | 7/2010 | Tzou et al. | 433/3 |
| 2010/0320405 A1 | 12/2010 | Gardner, III | |
| 2011/0024649 A1 | 2/2011 | Merkle | |

OTHER PUBLICATIONS

Admoni, M.M., et al. "Disinfection efficacy in an integrated ultraviolet light contact lens care system." *CLAO J.* Oct. 1994; 20(4): 246-8. Print.

Dolman, P.J., et al. "Contact lens disinfection by ultraviolet light." *American Journal of Ophthalmology*, Dec. 15, 1989;108(6):665-9.

"UV Kills These Bugs.", *Review of Optometry*. Dec. 15, 1999 v136 i12 p. 62.

"Device cleans, disinfects soft contact lenses in 15 minutes.", *Ophthalmology Times*., Apr. 15, 2004 v29 i8 p. 66.

PCT International Search Report, dated Nov. 15, 2011, for PCT Int'l Appln. No. PCT/US2011/036822.

* cited by examiner

OPHTHALMIC LENS DISINFECTING STORAGE CASE

RELATED APPLICATIONS

This application claims priority to Provisional U.S. Patent Application Ser. No. 61/346,152, filed on May 19, 2010.

FIELD OF USE

This invention describes a case for storing an ophthalmic lens and, more specifically, in some embodiments, a case with disinfecting functionality while storing an ophthalmic lens such as a contact lens.

BACKGROUND

It is well known that contact lenses can be used to improve vision. Various contact lenses have been commercially produced for many years. Early designs of contact lenses were fashioned from hard materials. Although these lenses are still currently used in some applications, they are not suitable for all patients due to their poor comfort and relatively low permeability to oxygen. Later developments in the field gave rise to soft contact lenses, based upon hydrogels.

Hydrogel contact lenses are very popular today. These lenses are often more comfortable to wear than contact lenses made of hard materials. Many hydrogel contact lenses may be worn for more than one day. However, a build-up of microbial life and bacteria on the lenses generally makes it desirable to periodically remove the lenses and disinfect them.

Disinfection of contact lenses traditionally entails placing the contact lens in a container or case and subjecting the contact lens to a chemical disinfectant. However, chemical disinfectants are not always as efficacious as may be desired. From time to time, a contact lens with a bacteria, mold, fungus or other type of adverse life form is reinserted into a user's eye with the result being a diseased eye. In addition, disinfecting solutions tend to be expensive and add to the total cost of using contact lenses for vision correction or cosmetic enhancement. New methods and approaches are therefore needed to disinfect contact lenses.

SUMMARY

Accordingly, the present invention includes an ophthalmic lens storage case for storing reusable contact lenses and disinfecting the lenses during the storage. The lens storage case is capable of receiving disinfecting radiation in a wavelength and intensity suitable to kill unwanted bacteria, viruses, molds, fungi and the like on a contact lens.

In addition, in some embodiments, the storage case is formed in a shape which mechanically communicates to receive vibrational frequencies at a frequency suitable to dislocate expired microbials and provide increased exposure of unexpired microbials to life extinguishing radiation.

In some preferred embodiments, a positioning artifact, such as, for example, a lens centering mechanism, is provided for positioning an ophthalmic lens stored in a radiation disinfecting ophthalmic lens case. Preferred positioning aligns the stored lens in a path of disinfecting radiation.

In another aspect, in some embodiments, a lens storage case according to the present invention includes one or more reflective surfaces for reflecting disinfecting radiation back at an ophthalmic lens stored in the storage case.

DETAILED DESCRIPTION OF THE INVENTION

The present invention includes methods and apparatus for disinfecting an ophthalmic lens. In addition, the present invention includes a storage case for holding an ophthalmic lens while it is disinfected with disinfecting radiation.

In the following sections, detailed descriptions of embodiments of the invention will be given. The description of both preferred and alternative embodiments are exemplary embodiments only, and it is understood to those skilled in the art that variations, modifications and alterations may be apparent. It is therefore to be understood that said exemplary embodiments do not limit the scope of the underlying invention.

Glossary

In this description and claims directed to the presented invention, various terms may be used for which the following definitions will apply:

Disinfecting Radiation: as used herein refers to a frequency and intensity of radiation sufficient to diminish the life expectancy of a life form receiving a Disinfecting Radiation Dose.

Disinfecting Radiation Dose: as used herein refers to an amount of radiation to reduce an amount of life by at least two logs on a logarithmic scale, and preferably three logs or more, wherein life includes at least bacteria, viruses, molds and fungi.

Disinfecting Radiation Source: as used herein refers to a device capable of generating disinfecting radiation at an intensity and for a duration necessary to disinfect a lens.

Lens: refers to any ophthalmic device that resides in or on the eye. These devices can provide optical correction or may be cosmetic. For example, the term lens can refer to a contact lens, intraocular lens, overlay lens, ocular insert, optical insert or other similar device through which vision is corrected or modified, or through which eye physiology is cosmetically enhanced (e.g. iris color) without impeding vision. In some embodiments, the preferred lenses of the invention are soft contact lenses made from silicone elastomers or hydrogels, which include but are not limited to silicone hydrogels, and fluorohydrogels.

Figure 1:
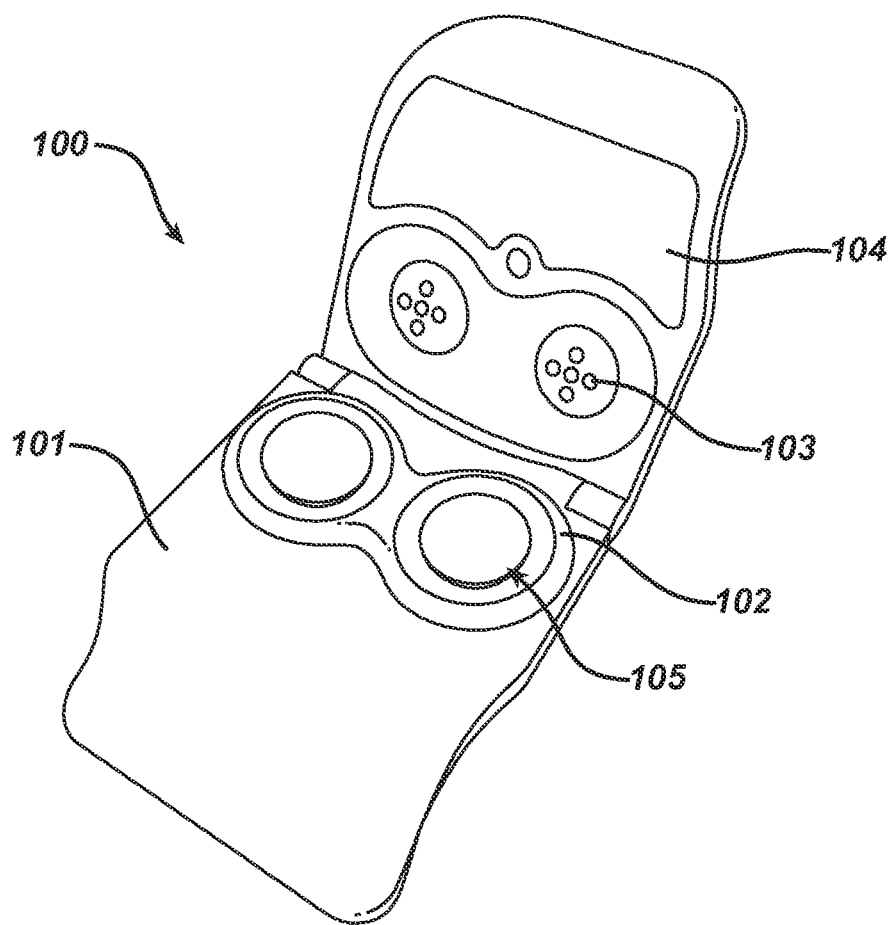
FIG. 1 illustrates a lens storage case in a base unit according to some embodiments of the present invention.

Referring now to FIG. 1, an ophthalmic lens disinfecting system 100 is illustrated including a radiation disinfecting base 101, a radiation disinfecting storage case 102 and a disinfecting radiation source 103. According to the present invention, a radiation disinfecting storage case 102 is positioned within the path of radiation from the disinfecting radiation source 103, such that one or more ophthalmic lenses stored within the radiation disinfecting storage case 102 are exposed to radiation emanating from the disinfecting radiation source 103 and life forms existing on, or in proximity to, the ophthalmic lenses are exposed to the radiation disinfecting radiation, provided by a disinfecting radiation source 103 and killed, essentially disinfecting the ophthalmic lens.

As illustrated, the radiation disinfecting storage case 102 is positioned in an open radiation disinfecting base 101. In some preferred embodiments, the radiation disinfecting storage case 102 includes a positioning artifact 105 for aligning the radiation disinfecting radiation source 103 with the radiation disinfecting storage case 102. As illustrated, the positioning artifact 105 such as a lens centering mechanism, includes an annular depression for receiving an annular arrangement of radiation from disinfecting radiation source 103. Positioning artifacts 105 may include almost any polygon shaped depression. Other embodiments may include one or more alignment pins. In still other embodiments, a positioning artifact 105 may include a snap, a threaded joining or other removably fixed type of joining.

In some embodiments, the positioning artifact 105 aligns the radiation disinfecting radiation source 103 in a position generally orthogonal to an apex of a contact lens stored within the radiation disinfecting storage case 102. In additional embodiments, a positioning artifact 105 aligns the radiation disinfecting radiation source 103 in a position generally orthogonal to a plane extending across a bottom perimeter of a contact lens.

In another aspect, in some embodiments, the positioning artifact may also be capable of transmitting a vibrational frequency from a radiation disinfecting base 101 to the radiation disinfecting storage case 102 and ultimately to a lens stored within the radiation disinfecting storage case 102. The vibrational frequency may be a frequency capable of causing expired life forms to be moved from within a path of radiation to an unexpired life form. Moving the expired life forms allows for more efficacious disinfecting by exposing more unexpired life forms to a direct path of radiation.

The disinfecting radiation source 103 may include one or more light emitting diodes (LEDs). In some preferred embodiments, the LEDs include ultraviolet (UV) emitting LEDs. Preferred embodiments include LEDs which emit light radiation with a wavelength of between about 250 nanometers of light radiation and about 280 nanometers of light radiation, preferably between 250 nanometers and 275 nanometers, and most preferably 254 nanometers.

Figure 2:
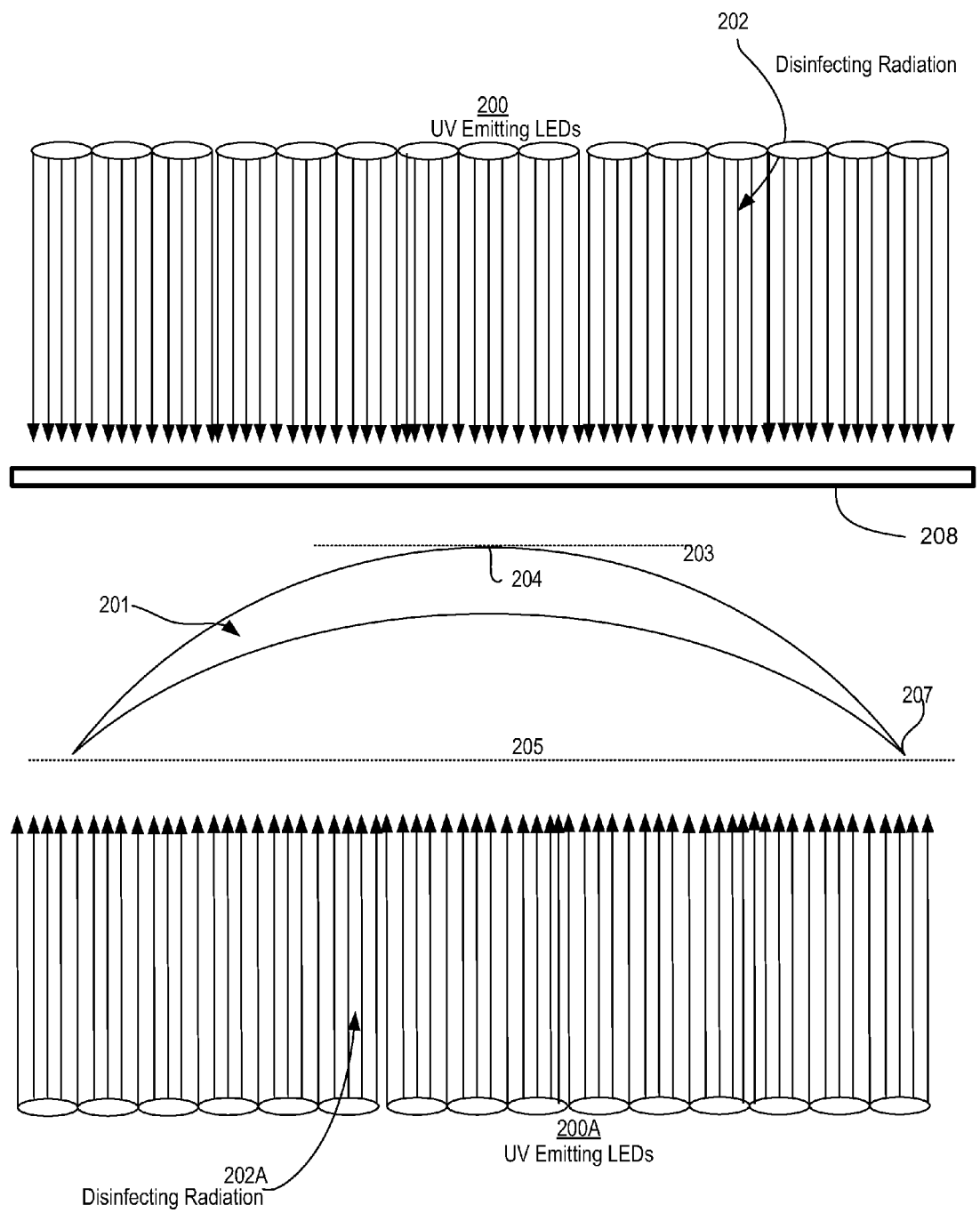
FIG. 2 illustrates some embodiments of alignment of a disinfecting radiation source with an ophthalmic lens in a lens storage case according to the present invention.

Referring now to FIG. 2, a block diagram illustrates some embodiments of alignment of a radiation disinfecting source 200, such as one or more UV LEDs radiating disinfecting radiation 202 in the UV spectrum towards a contact lens 201. In some preferred embodiments, UV LEDs will be arranged such that a radiation disinfecting storage case will align in a specific position in relation to the contact lens 201. The alignment is maintained via an alignment artifact. In some embodiments, a radiation disinfecting storage case is aligned to direct UV radiation 202 at an angle essentially orthogonal to a plane 203 touching an apex 204 of the contact lens 201 retained in a radiation disinfecting storage case.

In other embodiments, radiation disinfecting storage case may be aligned to direct disinfecting radiation 202A from one or more UV emitting LEDs 200A at an angle essentially orthogonal to a plane 205 across a perimeter edge 207 of the contact lens 201.

In another aspect, in some embodiments, one or more optics 208 may be used to focus disinfecting radiation onto a lens stored in a disinfecting radiation storage case. An optic may be included in a base or in a part of a storage case.

Figure 3:
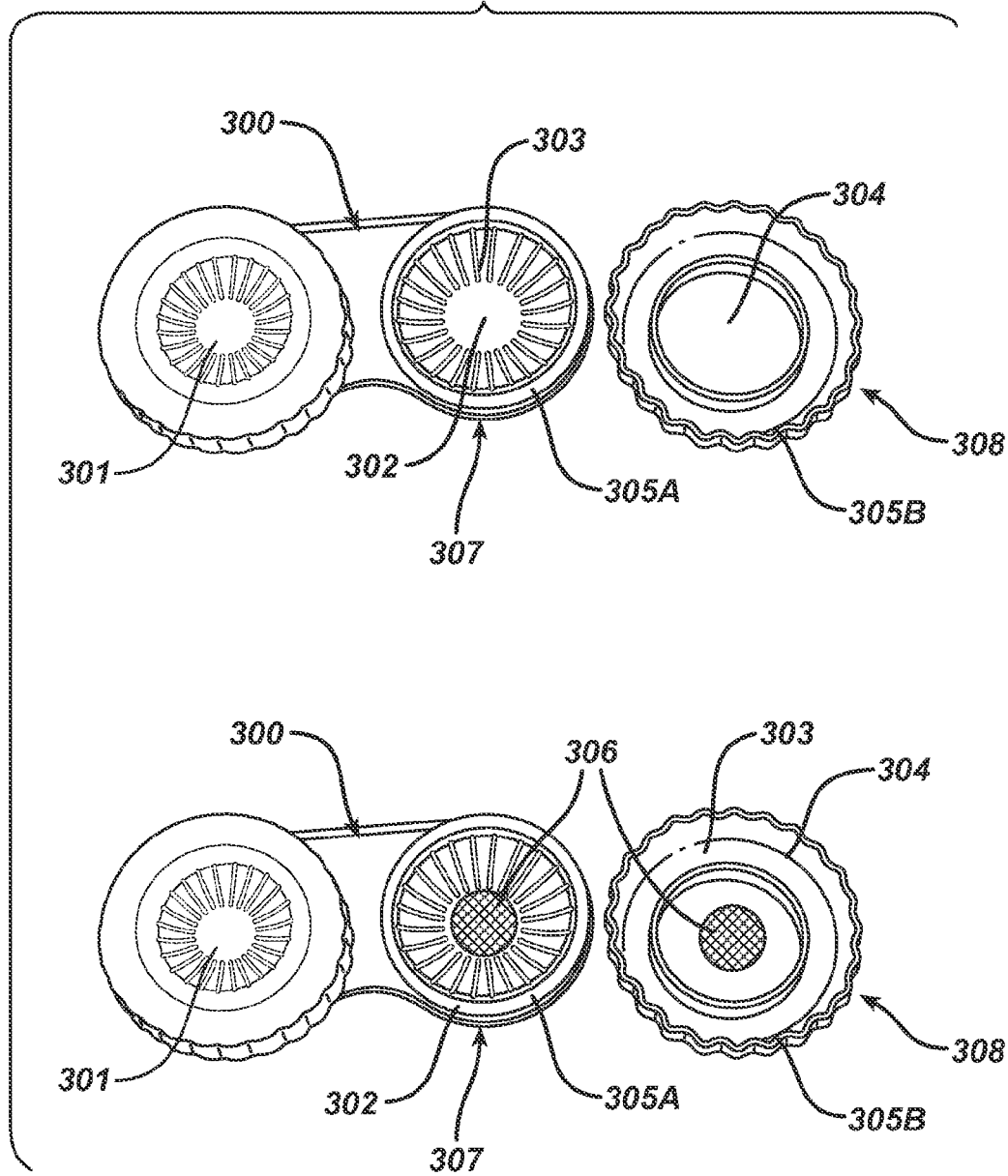
FIG. 3 illustrates a close up view of a storage case with one cap removed according to some embodiments of the present invention.

Referring now to FIG. 3, an exemplary a radiation disinfecting storage case 300 is illustrated. The radiation disinfecting storage case 300 includes one or more lens storage compartments 301. A storage compartment 301 is capable of receiving and storing one or more ophthalmic lenses, such as a contact lens.

Some embodiments include one or more lens alignment mechanisms 302 for positioning an ophthalmic lens stored in a storage compartment 301 included in a radiation disinfecting storage case 300. A lens alignment mechanism 302 may include for example a pedestal with an arcuate surface generally of a similar size and shape as an inside dimension of an ophthalmic lens. A convex surface may include an arc generally equivalent to an arc of a concave surface of an ophthalmic lens to be stored within the radiation disinfecting storage case. Other embodiments may include a lens alignment mechanism 306 comprising a bowl generally of a similar size and shape as an outside dimension of an ophthalmic lens.

Preferred positioning aligns the stored lens in a direct path of disinfecting radiation. However, other embodiments may include one or reflective surfaces 306. A reflective surface 306 may be generally proximate to, such as, in some embodiments, generally parallel to one or a convex surface of a stored lens or a concave lens surface.

Other embodiments may include a reflective surface 306 generally around a perimeter of a stored lens.

One or more radiation windows 303-304 are included in the storage compartments 301. The radiation windows 303-304 provide portions of the radiation disinfecting storage case that are at least partially transparent to wavelengths of disinfecting radiation. Preferably the radiation windows 303-304 will be as close to 100% transparent as possible to disinfecting radiation transmitted into the storage compartment 301. Plastics that are injection moldable may be 90% or more or even 98% or more transparent to UV radiation. Specific wavelengths may include between about 254 nanometers to 280 nanometers.

In some embodiments, a radiation window may also include an optic for directing disinfecting radiation towards areas of an ophthalmic lens stored in the stored compartment 301.

Examples of materials from which the radiation windows 303-304 may be formed include, cyclic olefins, TOPAS, ZEONOR or other injection moldable plastic.

Other plastics or glass may also be utilized as a material for the radiation window 303-304. The area of the radiation windows 303-304 should be sufficient to admit enough disinfecting radition into the storage compartments to kill life forms present on an ophthalmic lens stored in the storage compartment 301.

Some preferred methods of manufacture of a radiation disinfecting storage case include injection molding processes. Other methods include, for example, lathing, stereo lithography, and three dimensional printing.

In another aspect of the radiation disinfecting storage case 300, a fastening mechanism for securing and removing a cap 308 from a storage compartment 307. The fastening mechanism 305A-305B may include a threaded portion, a snap, a tapered joint of other mechanism for removably securing the cap 308 to the case at the discretion of the user. While the cap 308 is secured to the storage compartment 307, the cap seals off an ambient atmosphere from the storage compartment 307 and also contains an ophthalmic lens and, in some embodiments, a solution, such as, for example a saline solution, within the compartment 307.

Figure 4:
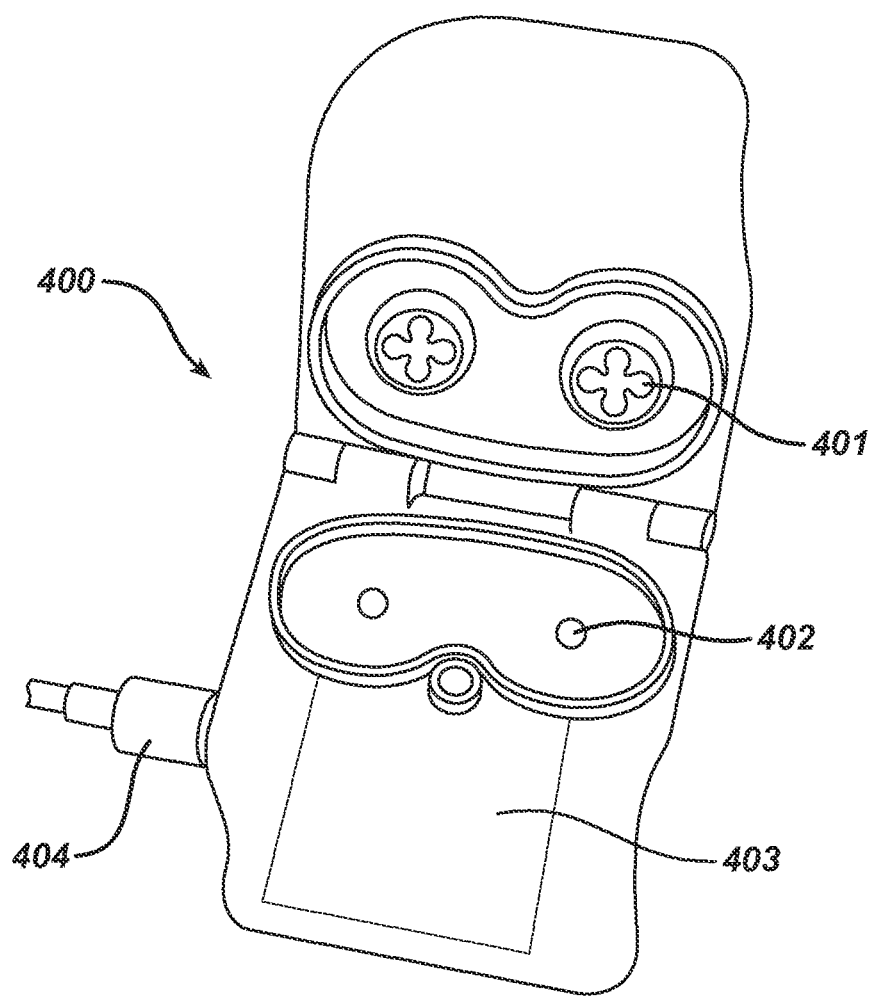
FIG. 4 illustrates aspects of a base unit that may be used in conjunction with a storage case according to some embodiments of the present invention.

Referring now to FIG. 4, a base unit 400 is illustrated with multiple disinfecting radiation source LEDs 401-402. As illustrated, the disinfecting radiation source LEDs 401-402 include overhead disinfecting radiation source LEDs 401 and lower disinfecting radiation source LEDs 402. Various embodiments may include one or both of overhead disinfecting radiation source LEDs 401 and lower disinfecting radiation source LEDs 402. In addition to the overhead disinfecting radiation source LEDs 401 and lower disinfecting radiation source LEDs 402, the base unit may include a processor board 403 with control electronics for controlling various aspects associated with the base unit 400. An electrical communication connector 404 may also be included in the base unit 400.

CONCLUSION

The present invention, as described above and as further defined by the claims below, provides methods and apparatus for disinfecting an ophthalmic lens.

The invention claimed is:

1. A storage case for storing one or more ophthalmic lenses during disinfecting via exposure to ultraviolet radiation, the storage case comprising:
   an ophthalmic lens storage compartment, wherein the ophthalmic lens storage container is capable of fitting in a personal disinfecting base, wherein the fitting allows for directed exposure of an ophthalmic lens to a radiation source included within the personal disinfecting base;
   a removable cap for sealing the storage compartment from an ambient atmosphere;
   one or more disinfection radiation windows comprising injection moldable plastic 90% or more transparent to disinfecting radiation passing through the disinfection window, wherein the disinfecting radiation comprises ultraviolet light in the range of about 254 nanometers to 280 nanometers; and
   an alignment mechanism for aligning the ophthalmic lens stored in the storage compartment in the path of the disinfection radiation window, wherein the alignment mechanism is capable of orienting the ophthalmic lens relative to the radiation source.

2. The storage case of claim 1 wherein the alignment mechanism comprises a pedestal.

3. The storage case of claim 2 wherein the pedestal comprises a convex surface comprising an arc generally equivalent to an arc of a concave surface of an ophthalmic lens to be stored within the storage case.

4. The storage case of claim 3 wherein the pedestal comprises a reflective surface, wherein the reflective surface is capable of reflecting disinfecting radiation from the disinfecting base to intersect with the surface of the ophthalmic lens at predefined angles.

5. The storage case of claim 1 wherein the alignment mechanism comprises a concave surface comprising an arc generally equivalent to an arc of a convex surface of an ophthalmic lens to be stored within the storage case.

6. The storage case of claim 1 additionally comprising an optic for directing disinfecting radiation towards an ophthalmic lens stored in the storage case.

7. The storage case of claim 6 wherein the storage compartment comprises the optic for directing disinfecting radiation towards the ophthalmic lens stored in the storage case.

8. The storage case of claim 6 wherein the removable cap comprises the optic for directing disinfecting radiation towards the ophthalmic lens stored in the storage case.

9. The storage case of claim 1 wherein the removable cap comprises at least one disinfection radiation window.

10. The storage case of claim 1 wherein the storage compartment comprises at least one disinfection radiation window.

11. The storage case of claim 1 wherein the removable cap comprises a fastening mechanism comprising a threaded portion.

12. The storage case of claim 1 wherein the removable cap comprises a fastening mechanism comprising a snap.

13. The storage case of claim 1 wherein the removable cap comprises a fastening mechanism comprising a tapered interface.

\* \* \* \* \*